(12) United States Patent
Chow et al.

(10) Patent No.: US 8,263,002 B1
(45) Date of Patent: Sep. 11, 2012

(54) FABRICATION OF ZNO NANOROD-BASED HYDROGEN GAS NANOSENSOR

(75) Inventors: Lee Chow, Orlando, FL (US); Oleg Lupan, Chisinau (MD); Guangyu Chai, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 548 days.

(21) Appl. No.: 12/465,043

(22) Filed: May 13, 2009

Related U.S. Application Data

(60) Provisional application No. 61/053,846, filed on May 16, 2008.

(51) Int. Cl.
G01N 27/04 (2006.01)
(52) U.S. Cl. ........................................................ 422/83
(58) Field of Classification Search .................. None
See application file for complete search history.

(56) References Cited

OTHER PUBLICATIONS

O. Lupan et al., Fabrication of ZnO Nanorod-Based Hydrogen Gas Nanosensor, 38 Microelectron. J. 1211-1216 (2007).*
O. Lupan et al., Focused-Ion Beam Fabrication of ZnO Nanorod-Based UV Photodetector Using the In-Situ Lift-Out Technique, 205 Phys. Stat. Sol. A 2673-2678 (2008).*
Raju, A., Rao, C., Gas-sensing Characteristics of ZnO and Copper-Impregnated ZnO, Sensors and Actuators B, 1991, pp. 305-310, vol. 3, No. 4, Abstract.
Lupan, O., Chow, L., Synthesis and Characterizations of ZnO Nanorods Arrays and Mesoporous Films for Device Applications, NSTI-Nanotech, 2007, pp. 457-460, vol. 4.
Lupan, O., Chow, L., Chai, G., Roldan, B., Naitabdi, A., Schulte, A., Heinrich, H., Nonofabrcation and Characterization on ZnO Nanorod Array abd Branched mirorods by Aqueous Solution Route and Rapid Thermal Processing, Materials Science and Engineering B, 2007, pp. 57-66, vol. 145.
Chai, G., Chow, L., Zhou, D., Byahut, S., Foucused-Ion-Beam assisted Fabrication of Individual Multiwall Carbon Nanotube Field Emitter, Science Direct, 2005, pp. 2083-2087.
Chen, J., Herricks, T., Xia, Y., Polyol Synthesis of Platinum Nanostructures: Control of Morphology through the Manipulation of Reduction Kinetics, Angew. Chem. Int. Ed., 2005, pp. 2589-2592, vol. 44.
Galoppini, E., Rochford, J., Chen, H., Saraf, G., Lu, Y., Hagfeldt, A., Boschloo, G., Fast Electron Transport in Metal Organic Vapor Deposition Grow Dye Sensitized ZnO Nanorod Solar Cells, the Journal of Physical Chemistry B, pp. 16159-16161, vol. 110, No. 33.
Pasquier, A., Chen, H., Lu, Y., Dye Sensitized solar Cells using Well-Aligned Zinc Oxide and Nanotip Arrays, Applied Physics Letters, 2006, pp. 253513.1-253513.3, vol. 89.
Wang, C., Chu, X., Wu, M., Detection of H2S Down to ppb Levels at Room Temperature using Sensor Based on ZnO Nanorods. Sensors and Actuators B, 2006, pp. 320-323, vol. 113.
Huang, X., Choi, Y., Chemical Sensors Based on Nanostructure Materials, Sensors and Actuators, 2007, pp. 659-671, vol. 122.
Pasquier, A., Chen, H., Lu, Y., Dye Sensitized Solar Cells Using Well-Aligned Zinc Oxide Nanotip Arrays, Applied Physics Letters, 2006, pp. 25313.1-25313.3, vol. 89.
Kang, B., Heo, Y., Norton, D., Rem, F., Gila, B., Pearton, S., Hydrogen and Ozone Gas Sensing Using Multiple ZnO Nanorod. Applied Physics A, pp. 1029-1032, vol. 80, (2005).
Tien, L., Sadik, P., Norton, D., Voss, L., Pearton, S., Wang, H., Kang, B., Ren, F., Jun, J., Lin, J., Hydrogen Sensing at room Temperature with Pt-Coated ZnO Thin Films and Nanorods, 2005, pp. 222106.1-222106.3, vol. 87.
Kang, B., Heo, Y., Tien, L., Norton, D., Ren, F., Gila, B., Pearton, S., Hydrogen Ozone gas Sensing using Multiple ZnO Nanorods, Applied Physics A, 2005, pp. 1029-1032, vol. 80.
Basu, S., Dutta, A., Room Temperature Hydrogen Sensors based on ZnO, Materials Chemistry and Physics, 1997, pp. 93-96, vol. 47.
Favier, F., Wakter, E., Zach, M., Benter, T., Peener, R., Hydrogen Sensors and Switches from Electrodeposited Palladium Mesowire Arrays, 2001, pp. 2227-2230, vol. 293.
Wang, J., Sun, X., Yang, Y., Huang, H., Lee, Y., Tan, O., Vaysseres, L., Hydrothermally Grown Oriented ZnO Nanorod Arrays for Gas Sensing Application, Nanotechnology, 2006, pp. 4995-4998, vol. 17.
Sun, Z., Liy, L, Zhang, L., Jia, D., Rapid Synthesis of ZnO Non-Rods by One-Step, Room-Temperature, Solid-State Reaction and Their Gas-Sensing Properties, Nanotechnology, 2006, pp. 2266-2270, vol. 17.
Look, D., Recent Advances in ZnO Materials and Devices, Materials Science and Engineering B, 2001, pp. 383-387, vol. 80.
Rout, C., Kulkarni, G., Rao, C., Room Temperature Hydrogen and Hydrocarbon Sensors Based on Single Nanowires of Metal Oxide, Journal of physics D: Applied Science, 2007, pp. 2777-2782, vol. 40.
Yi, G., Wang, C., Park, W., ZnO Nanoroda: Synthesis, Characterization and Applications, Semiconductor Science and Technology, 2005, pp. S22-S34, vol. 20.
Liao, L., Lu, H., Li, J., He, H., Wang, D., Fu, D., Liu, C., Zhang, W., Size Dependence of Gas Sensitivity of ZnO Nanorods, The Journal of Physical Chemistry C, 2007, pp. 1900-1903, vol. 111, No. 5.
Ozgur,U., Alivov, Y., Liu, C., Teke, A., Reshchikov, M., Dogan, S., Avrutin, V., Cho, S., Morkoc, H., A Comprehensive Review of ZnO Materials and Devices. Journal of Applied Physics, 2005, pp. 041301.1-041301.103, vol. 98.
Dresselhouse, et al., Basic Research Needs for the Hydrogen Economy, Office of Science, 2003, pp. 1-160.

* cited by examiner

Primary Examiner — Randy Boyer
(74) Attorney, Agent, or Firm — Brian S. Steinberger; Joyce Morlin; Law Offices of Brian S. Steinberger, P.A.

(57) ABSTRACT

The nanofabrication of a hydrogen gas nanosensor device from single straight and branched, tripod shaped ZnO nanorods using in-situ lift-out technique, performed in the chamber of a focused ion beam (FIB) system is disclosed. Self-assembled ZnO branched nanorods have been grown by a cost-effective and fast synthesis route using an aqueous solution deposition method and rapid thermal processing. The properties of the ZnO nanorod structures were analyzed by X-ray diffraction, scanning electron microscopy, energy dispersion X-ray spectroscopy, transmission electron microscopy and micro-Raman spectroscopy. High quality ZnO nanorods were obtained with a 90% success rate for building nanodevices. The fabricated nanosensor can gauge 150 ppm hydrogen gas in the air at room temperature. The nanosensor has selectivity for other gases such as oxygen, methane, carbon monoxide and liquid propane gas. The ZnO nanorod sensors of the present invention also operate at low power of less than 5 microwatts.

8 Claims, 10 Drawing Sheets

FABRICATION OF ZNO NANOROD-BASED HYDROGEN GAS NANOSENSOR

This invention claims the benefit of priority based on the U.S. Provisional Patent Application Ser. No. 61/053,846 filed May 16, 2008 and is incorporated herein by reference.

FIELD OF THE INVENTION

This invention relates to hydrogen sensors, in particular to hydrogen gas sensors, devices and methods of fabrication, based on zinc oxide (ZnO) nanorods or nanowires that gauge the presence of hydrogen and other gases used in solid oxide fuel cells for space craft, hydrogen engine cars and other vehicles.

BACKGROUND AND PRIOR ART

Hydrogen gas is a very desirable fuel because it can be reacted with oxygen in hydrogen-consuming devices, such as a fuel cell, combustion engine or gas turbine, to produce energy and water. The use of hydrogen gas can ameliorate environmental pollution; lessen the world's dependency on fossil fuels or petroleum; ease fears of depleted energy sources.

Hydrogen ($H_2$) is expected to be the principal energy source or "the fuel of the future" and can be used in $H_2$ engine cars and future power devices, as described in "Basic Research Needs for the Hydrogen Economy," Report of the Basic Energy Sciences Workshop on Hydrogen Production, Storage, and Use, May 13-15, 2003, http://www.sc.doe.gov/bes/besacBasicResearch_Needs_To_Assure_A_Secure_Energy_Future, second printing, February 2004.

Some of the future power devices include solid oxide fuel cells as reported by H. T. Wang et al. in "Hydrogen-selective sensing at room temperature with ZnO nanorods," *Appl. Phys. Lett.* 86 (2005) 243503-243505 and L. C. Tien et al. in "Hydrogen sensing at room temperature with Pt-coated ZnO thin films and nanorods," *Appl. Phys. Lett.* 87 (2005) 222106-222108. However, $H_2$ is a hazardous, odorless, and highly inflammable gas and it is very important to detect its leakage. A reliable and inexpensive sensor that can take advantage of nanoscale technology to detect hydrogen leaks is the focus of many research groups including H. T. Wang et al., *Appl. Phys. Lett.* 86, supra. L. C. Tien et al. *Appl. Phys. Lett* 87, supra, B. S. Kang, in "Hydrogen and ozone gas sensing using multiple ZnO nanorods," *Appl. Phys. A* 80 (2005) 1029-1032, J. X. Wang, et al. in "Hydrothermally grown oriented ZnO nanorod arrays for gas sensing applications," *Nanotechnology* 17 (19) (2006) 4995-4998, F. Favier, et al. in "Hydrogen sensors and electrodeposited palladium mesowire arrays, *Science* 293 (2001) 2227-2231, and G. C. Yi et al. in "ZnO nanorods: synthesis, characterization and applications, *Semicond. Sci. Technol.* 20 (2005) S22-S34.

Common sensors propose use of an indirect approach (e.g. Raman spectroscopy, etc.) or requiring complicated components to detect the presence of $H_2$. Many ideas have been proposed such as use of different metal wires, semiconductor oxides nanoarchitectures, and the like. Gas sensors based on ZnO nanorods, $SnO_2$ nanowires, $In_2O_3$ nanowires, etc. showed excellent response and recovery characteristics, as reported by L. Liao et al. in "Size dependence of gas sensitivity of ZnO nanorods," *J. Phys. Chem. C* 111 (5) (2007) 1900-1903 and can potentially overcome obstacles of other types of sensors, such as sensitivity, selectivity, and the like.

Among different nanomaterials, nano-ZnO is one of the most promising multifunctional materials for gas sensors, especially for $H_2$ sensing. ZnO nanorods also have the advantages of large surface area, radiation hardness, as reported by D. C. Look in "Recent advances in ZnO materials and devices, *Mater. Sci. Eng. B* 80 (2001) 383-387, thermal and mechanical stability, as discussed by Ü. Özgür et al. in "Comprehensive review of ZnO materials and devices," *J. Appl. Phys.* 98 (2005) 041301. Properties of the nano-ZnO materials depend on the microstructures including morphology, crystal size, orientation, aspect ratio, and crystalline density, according to Z. R. Tian et al. in "Complex and oriented ZnO nanostructure, *Nat. Mater.* 2 (12) (2003) 821-826.

Sensing properties of nano-ZnO are directly related to its preparation history, particle size, surface to volume ratio, morphology, and operating temperature. The signal consists of conductivity changes due to gas adsorption on the surface and permits real-time detection.

Recently, the branching growth phenomena such as nanojunction arrays have attracted great interest for achieving high degree of superior functionality via direct self-assembly. Thus, multiple ZnO nanorods, as discussed by B. S. Kang et at in *Appl. Phys. A* 80, supra and single ZnO two-dimensional branched nanorods have attracted considerable attention due to their unique properties that strongly depend on their size, morphologies reported by J. Y. Chen, et al. in *Angew. Chem. Int. Ed* 44 (2005) 2589 and configurations reported by O. Lupan, et al. in "Synthesis and characterizations of ZnO nanorods arrays and mesoporous films for device applications, in *Proceedings of NSTI Nanotechnology Conference and Trade Show*, Santa Clara, Calif., USA, 20-24 May 2007, V. 4, 457-460; and O. Lupan et al. in "In-situ lift-out fabrication and characterizations of ZnO branched nanorod-based sensors," *Proceedings of NSTI Nanotechnology Conference and Trade Show*, Santa Clara, Calif., USA, 20-24 May 2007, and their possible use as low-dimensional building blocks or functional units in $H_2$ nanosensors and nanodevices, according to G. C. Yi in *Semicond. Sci. Technol.* 20, supra and Z. P. Sun et al. in "Rapid synthesis of ZnO nanorods by one-step, room-temperature, solid-state reaction and their gas-sensing properties," *Nanotechnology* 17 (2006) 2266-2270.

Different $H_2$ sensors have been demonstrated. Wang et al. in *Appl. Phys. Lett.* 86, supra used multiple ZnO nanorods with Pd and achieved 4.2% relative response ($\Delta R/R$) at 500 ppm $H_2$ in $N_2$ after 10 minutes exposure.

According to experimental results presented by Wang et al. *Nanotechnology* 17, supra the $H_2$ sensitivity of nanowires has the highest sensitivity (S~8) at 250° C. Tien et al. in "Room-temperature hydrogen-selective sensing using single Pt-coated ZnO nanowires at microwatt power levels," *Electrochem. Solid-State Lett.* 8 (9) (2005) G230-G232 used single Pt-coated ZnO nanowires and achieved a relative response of ~20% at 500 ppm $H_2$ in $N_2$ after 10 minute exposure. At the same time realized sensitivity ($S_{max}=R_{air}/R_{H2}$ is between 1 and 2) at 100 ppm $H_2$ with ZnO nanorods is several times higher than the sensitivity of ZnO films at 300-400° C. obtained by Y. Min et al. in "Gas response of reactively sputtered ZnO films on Si-based micro-array," *Sens. Actuators B: Chem.* 93 (1-3) (2003) 435-441.

Tien et al. *Appl. Phys. Lett.* 87, supra demonstrated a current response of a factor ~3 times larger for Pt-coated multiple ZnO nanorods versus ZnO thin films upon exposure to 500 ppm $H_2$ in $N_2$ at room temperature. Tien et al. also found that the ZnO multiple nanorods sensors showed a faster response and a slower recovery in air after $H_2$ exposure than ZnO films.

Single nanowires of different metal oxides are discussed By C. S. Rout, et al in "Room temperature hydrogen and hydrocarbon sensors based on single nanowires of metal oxides," *J. Phys. D: Appl. Phys.* 40 (2007) 2777-2782 and metal catalyst coatings (Pt, Pd, Au, Ag, Ti and Ni) on multiple ZnO nanorods which are easy to fabricate and possess enhanced sensing properties are reported by H. T. Wang et al in "Detection of hydrogen at room temperature with catalyst-coated multiple ZnO nanorods," *Appl. Phys. A: Mater. Sci. Process.* 81 (6) (2005) 1117-1119.

Although ZnO nanorods sensors had a high response, high selectivity, and short response time to low concentrations of gas, at the current stage, it is still difficult to obtain single nanowire and to fabricate this kind of device in large quantities according to C. Wang in "Detection of $H_2S$ down to ppb levels at room temperature using sensors based on ZnO nanorods, *Sens. Actuators B* 113 (1) (2006) 320-323.

In the sensor development field some of the considerations are increased complexity, lengthy sample preparation and device fabrication, time consuming analysis and selectivity. Thus, for wide applications of ZnO nano/microrods in sensors, an inexpensive and environmentally benign self-assembly synthesis process is required in order to synthesize transferable nanorods which can be easily handled with modern equipment.

The latest research efforts are directed towards obtaining alternative, lightweight and flexible nanodevices as pointed out by E. Galoppini et al. in "Fast electron transport in metal organic vapor deposition grown dye-sensitized ZnO nanorod solar cells, "*J. Phys. Chem. B* 110 (2006) 16159-16161 and A. Du Pasquier, et al. in "Dye sensitized solar cells using well-aligned zinc oxide nanotip arrays," *Appl. Phys. Lett* 89 (2006), 253513.

The present inventors have published the following journal article, Oleg Lupan et al. in "Fabrication of ZnO nanorod-based hydrogen gas nanosensor," in *Microelectronics Journal* 38 (2007) pages 1211-1216 which appeared after the filing of U.S. provisional patent application Ser. No. 61/053,846, filed May 16, 2008; both the publication and the U.S. provisional patent application Ser. No. 61/053,846 are incorporated herein by reference.

The present invention is focused on the fabrication of single and branched (tripod) ZnO nanorods as the material template for designing a $H_2$ sensor. The present invention also provides a synthesis route for self-assembled ZnO nanorods easily transferable to other substrates and in-situ lift-out techniques using focused ion beam (FIB) system to fabricate individual nanosensor with at least one electrode, for a single ZnO nanorod, or three electrodes for a branched, tripod shaped ZnO nanorod, to detect $H_2$ at room temperature and provide a sensor that is quite selective in sensing $H_2$ in an environment with other gases.

SUMMARY OF THE INVENTION

The first objective of the present invention is to provide a method for fabrication of self-assembled ZnO branched nanorod hydrogen nanosensor using in-situ lift-out technique in focused ion beam (FIB) system with three electrodes to detect hydrogen gas at room temperature.

The second objective of the present invention is to provide a method for fabrication of a single ZnO nanorod gas nanosensor using in-situ lift-out technique that is very selective in the detection of hydrogen gas at room temperature.

The third objective of the present invention is to provide a method for synthesis of ZnO nanorods and self-assembled ZnO branched nanorods that permits individual and branched nanorods to be easily transferred to other substrates.

The fourth objective of the present invention is to provide a self-assembled ZnO branched nanorod to be used in a technique that permits using the focused ion beam (FIB) system for handling.

The fifth objective of this invention is to provide a method for fabrication of self-assembled ZnO branched nanorod gas sensors that are easy to replicate, cost effective, selectively sensitive to $H_2$, with quick response and quick recovery time.

A preferred process for producing self-assembled ZnO nanorod structures through low-temperature aqueous solution deposition on substrates consists of immersing a substrate surface in a solution of stannous chloride ($SnCl_2$), water and hydrochloric acid (HCl), removing the substrate surface from the solution and rinsing the substrate surface with water, placing the rinsed substrate surface in an aqueous complex solution reactor containing a mixture of zinc sulfate, ammonium hydroxide and water, mounting the aqueous complex solution reactor with the rinsed substrate surface and the mixture of zinc sulfate, ammonium hydroxide and water on a pre-heated laboratory oven, maintaining the pre-heated laboratory oven at 90 degrees C. for ten minutes to support a heterogeneous reaction that produces a plurality of self-assembled, non-agglomerated, zinc oxide nanorod structures on the substrate surface, removing the substrate from the aqueous complex solution reactor and dipping the substrate surface in water to remove unreacted products from the surface of the plurality of self-assembled, non-agglomerated zinc oxide nanorod structures, and drying the substrate surface with the plurality of self-assembled, non-agglomerated zinc oxide nanorod structures in air at 150 degrees C.

The preferred substrate surface is selected from glass, silicon, silicon dioxide and mixtures thereof. The preferred water is deionized water.

It is also preferred that the mixture of zinc sulfate, ammonium hydroxide and water consists of 0.01-0.04 M of zinc sulfate and 29.6 weight % ammonium hydroxide and 30 ml of deionized water.

A more preferred process for producing self-assembled ZnO nanorods further includes a rapid thermal processing of the air dried plurality of self-assembled zinc oxide nanorod structures, wherein the rapid thermal processing includes heating at 650 degrees C. for approximately 60 seconds in an inert gas under ambient conditions.

The preferred shape of the plurality of ZnO nanorod structures are at least one of single straight nanorod and a branched, tripod shaped nanorod and the plurality of self-assembled zinc oxide nanostructures are prepared in a time period ranging from approximately 7 to approximately 15 minutes, preferably, in approximately ten minutes.

A preferred process for fabricating a zinc oxide nanorod hydrogen sensor using focused ion beam (FIB) in-situ lift-out technique, consists essentially of mounting a micromanipulator with a focused ion beam (FIB) needle adjacent to a nanosensor template surface consisting of a glass substrate with at least two pre-deposited, external aluminum (Al) electrodes, using a microscope and a micromanipulator to separate a plurality of individual zinc oxide nanorod structures formed on a first substrate surface, using the micromanipulator to arrange one of the plurality of individual zinc oxide nanorod structures on the nanosensor template surface by contacting the individual zinc oxide nanorod structure with the tip of an FIB needle on the first substrate surface where the plurality of zinc oxide nanorod structures are formed, attaching a first intermediate straight zinc oxide nanorod linearly to the tip of the FIB needle, then linearly attaching a second selected zinc oxide nanorod to the intermediate zinc oxide nanorod, raising the FIB needle and thereby moving the attached first intermediate zinc oxide nanorod and the second selected zinc oxide nanorod onto the nanosensor template with at least two pre-deposited external electrodes, positioning the second selected zinc oxide nanorod on the nanosensor template and fixing the second selected zinc oxide nanorod to at least one of the predeposited external electrodes of the nanosensor template, separating the first intermediate zinc oxide nanorod from the second selected zinc oxide nanorod that is fixed to at least one electrode of the nanosensor template, lifting the FIB needle and the attached first intermediate single zinc oxide nanorod away from the nanosensor template, and thereby, fabricating a room temperature, zinc oxide nanorod based hydrogen gas sensor on the nanosensor template surface.

The preferred means for attaching the first intermediate straight zinc oxide nanorod linearly to the tip of the FIB needle is by platinum (Pt) deposition welding and the preferred means for linearly attaching the second selected zinc oxide nanorod to the intermediate zinc oxide nanorod is by platinum (Pt) deposition welding.

The preferred shape of the second selected zinc oxide nanorod is at least one of a single, straight zinc oxide nanorod and a branched, tripod-shaped zinc oxide nanorod. It is also preferred to cut a square hole in the nanosensor template to increase the sensitivity of the zinc oxide nanorod-based nanosensor and it is also preferred that the micromanipulator place the second selected zinc oxide nanorod over the square hole in the nanosensor template.

Preferably, the zinc oxide nanorod nanosensor template has three electrode connections for attachment of the branched, tripod-shaped nanorod to detect hydrogen gas at room temperature.

The preferred zinc oxide hydrogen gas nanosensor is fabricated in a time period ranging from approximately 30 to approximately 45 minutes and provides a novel zinc oxide nanosensor device for the detection of hydrogen gas when fabricated by the process disclosed herein.

Further objects and advantages of this invention will be apparent from the following detailed description of a presently preferred embodiment that is illustrated schematically in the accompanying drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

The present invention provides the synthesis and characterizations of zinc oxide (ZnO) single and branched nanorods that are used for hydrogen sensors.

ZnO branched nanorods have been synthesized using aqueous solution deposition on glass or silicon (Si) substrates cleaned using a procedure described by O. Lupan et al. in *Proceedings of NSTI Nanotechnology Conference and Trade Show*, 20-24 May, 2007, supra and O. Lupan et al. in "Nanofabriction and characterization of ZnO nanorod arrays and branched microrods by aqueous solution route and rapid thermal processing," *Mater. Sci. Enz. B.,* 145, (2007) 57-66.

Starting materials are zinc sulfate and ammonia solution, all analytical grade (Fisher Scientific Corp.) without further purification. $Zn(SO4) \cdot 7H_2O$ (0.01-0.04 M) and $NH_4OH$ (29.6%) were mixed with 30 ml de-ionized (DI) water (~18.2MΩcm). The substrates were kept in solution of 0.2 g $SnCl_2$ in 200 ml DI water with 10 µl HCl for 3 minutes (min) then were rinsed with a jet of deionized (DI) water. After this procedure the substrates were placed in aqueous complex solution reactor and mounted on pre-heated laboratory oven and kept at 90° C. for 10 min. The oven then was turned off and the system was allowed to cool to 40° C. naturally. Then the substrates were dipped in DI water to remove unreacted products from nanorods surface and then dried in air at 150° C. for 5 min and subjected to rapid thermal processing at 650° C. for 60 seconds (s) at ambient conditions; the morphology of nanorod structures includes single nanorods and branched nanorods having a tripod structure.

The crystal structures of ZnO branched nanorods were investigated by X-ray diffraction (XRD; Rigaku 'DB max') and transmission electron microscopy (FEI Tecnai F30 TEM) at an accelerating voltage of 300 kV. The elemental analyses were examined using energy dispersion X-ray spectroscopy (EDX) and the morphologies of the nanorods by scanning electron microscope (SEM) Hitachi S800. These investigations confirmed that these nanorods are highly crystalline and regularly distributed throughout the substrate surface. For hydrogen detection using the ZnO branched nanorod, a measuring apparatus consisting of a closed quartz chamber connected to a gas flow system was assembled. The concentration of test gases was measured using pre-calibrated mass flow controller. Hydrogen and air were introduced to a gas mixer using separate mass flow controllers. The mixed gas was injected to a chamber in which the nanosensor was placed. A computer with suitable Lab-View interface handled all controls and acquisition of data.

Figure 1:
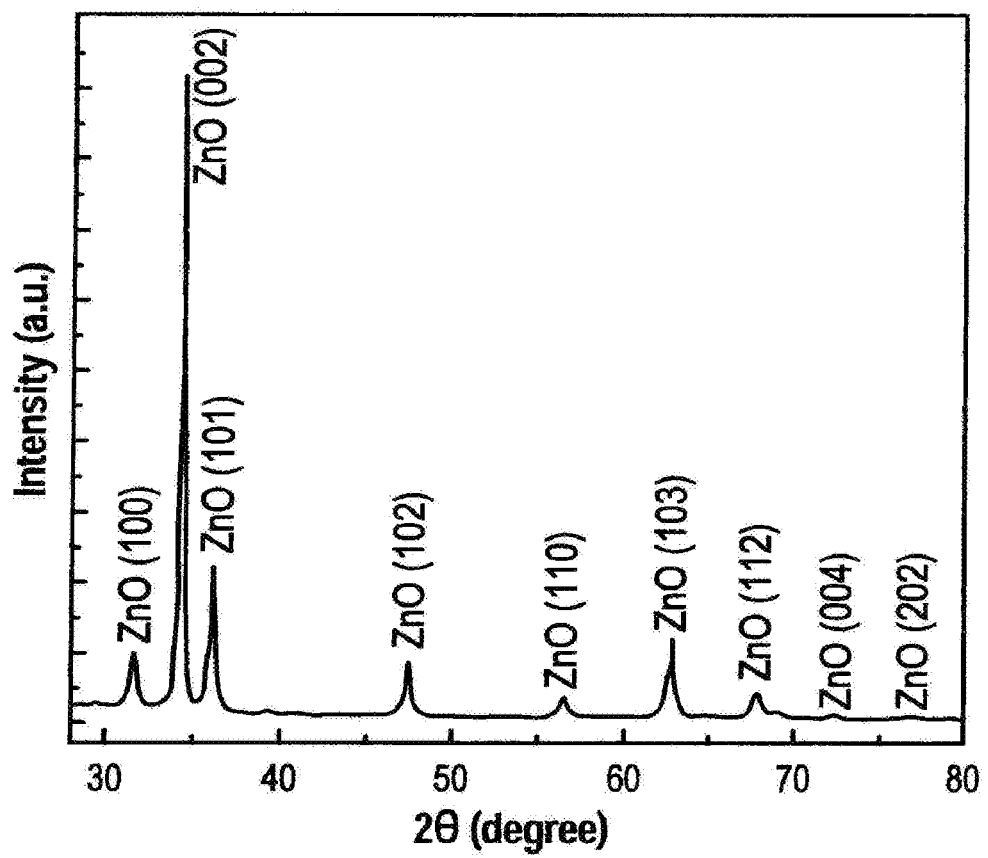
FIG. 1 shows the x-ray diffraction (XRD) pattern of the ZnO branched nanorods synthesized by aqueous solution method.

In FIG. 1, the X-ray diffraction (XRD) pattern of ZnO branched nanorods is shown, the diffraction peaks in the pattern are indexed to hexagonal wurtzite structured ZnO (space group: $P6_3mc(186)$; a=0.3249 nm, c=0.5206 nm) and the data are in agreement with JCPDS card for ZnO reported by the Joint Committee on Powder Diffraction Standards, Powder Diffraction File No. 36-1451.

The grown ZnO rods were also confirmed by the 1.0:1.0 stoichiometric composition deduced from the EDX analysis in all samples. TEM, XPS and micro-Raman characterization results have been discussed in detail by O. Lupan et al. in *Proceedings of NSTI Nanotechnology Conference and Trade Show,* 20-24 May, 2007, supra and O. Lupan et al. *Mater. Sci. Eng. B.,* 145, (2007) 57-66, supra.

Figure 2A:
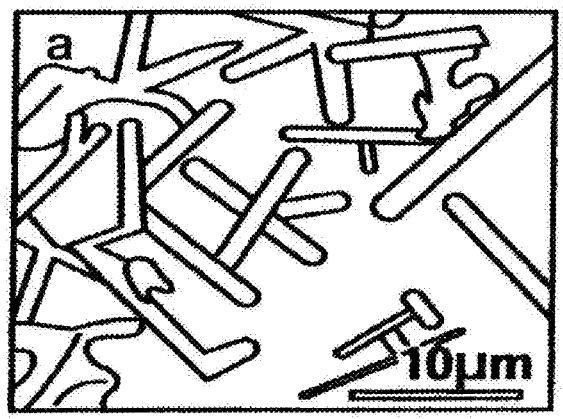
FIG. 2A is a drawing of a scanning electron microscopy (SEM) image of aqueous solution synthesized ZnO showing branched nanorods on initial glass substrate.
Figure 2B:
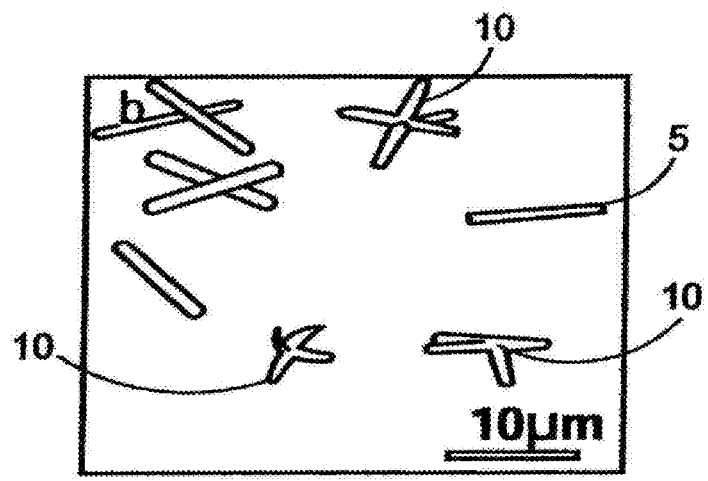
FIG. 2B is a drawing of a scanning electron microscopy (SEM) image of an aqueous solution synthesized ZnO showing single and branched nanorods transferred to $Si/SiO_2$ substrate and distributed on the surface in order to be picked up by the in-situ lift-out needle in the focused ion beam FIB/SEM system.
Figure 2C:
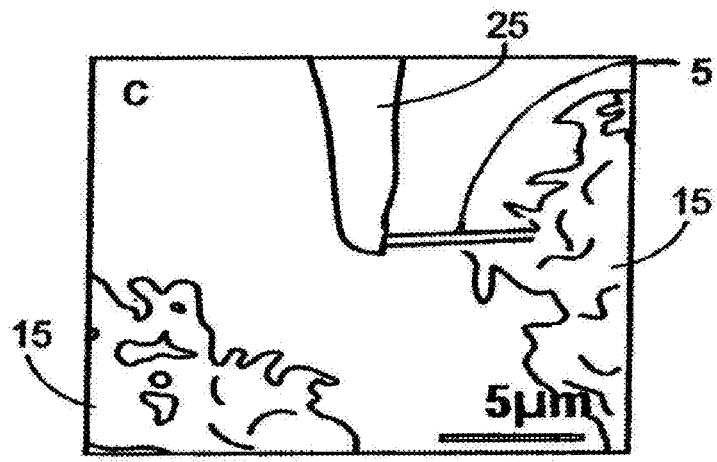
FIG. 2C is a drawing of a scanning electron microscopy (SEM) image of aqueous solution synthesized ZnO showing an attempt to pick up an individual nanorod from an agglomeration of ZnO nanorods.

Typical SEM images of ZnO branched nanorods are shown in FIGS. 2A-2C. A close observation (FIG. 2A) reveals that the individual ZnO nanorod has a radius of about 200 nm and length about 12-17 µm after 10 minute synthesis.

FIG. 2A is a perspective view of branched nanorods on an initial glass substrate.

FIG. 2B shows single 5 and branched 10 nanorods transferred to a Si/SiO substrate wherein the rods are distributed on the surface in order to be picked up by the in-situ, lift-out needle in the focused ion beam/scanning electron microscopy (FIB/SEM) system.

FIG. 2C shows a lift-out needle 25 attempting to pick up an individual nanorod 5 from an agglomeration of ZnO nanorods 15.

Lowering the concentration of ammonia hydroxide and controlling the reaction process permits the growth of smaller ZnO nanorods with radii less than 100 nm each, but smaller nanorods were difficult to be transferred, separated and picked-up in the FIB system as shown in FIG. 2C where there is an agglomeration of ZnO nanorods 15.

According to experimental results, the branched nanorods 10 shown in FIG. 2B, obtained by the process of the present invention, can be easily transferred to other $Si/SiO_2$ substrates and distributed on the surface of another substrate for further processing by the in-situ lift-out needle 25.

Example 1

Nanofabrication of Sensors by In-Situ Lift-Out Technique

In the following section, the in-situ lift-out technique is described. The $Si/SiO_2$ wafers were used as intermediate substrate for ZnO tripods transferring and distribution in order to avoid charging problems in the FIB system. For the nanosensor preparation, the glass substrate was used and aluminum (Al) electrodes were deposited as templates with external electrodes/connections.

Usually a microscope and a micromanipulator for the ex-situ lift-out technique have been used to separate individual ZnO nanorods in order to be easily attached to the in-situ FIB needle. A magnification of ×100 was used to separate ZnO nanorods transferred to intermediate $Si/SiO_2$ substrate and to distribute them on the surface for an easy pick-up. A magnification of ×6500 was used to position a needle 25 on the ion optic axis and to lift the single ZnO branched nanorod-tripod away from the $Si/SiO_2$ substrate.

A micromanipulator mounted beside the stage used permits movements in the nanometer regions along the x, y or z directions. A sample on the stage can be independently rotated perpendicular to an ion beam, which enables the easy arrangement of single ZnO branched nanorod on the nanosensor template with Al contacts as external electrodes.

In the in-situ process described by G. Chai, at al, in "Focused-ion-beam assisted fabrication of individual multi-wall carbon nanotube field emitter," *Carbon* 43 (2005) 2083-2087, attaching a single intermediate straight nanorod 20 on the FIB needle 25 (FIG. 3A) allows an easy pick-up of the branched nanorod 10 for further handling. This intermediary straight nanorod 20 can greatly enhance the nanofabrication capability and reduce the number of steps in the procedure and the total time for nanodevice fabrication, respectively.

Figure 3A:
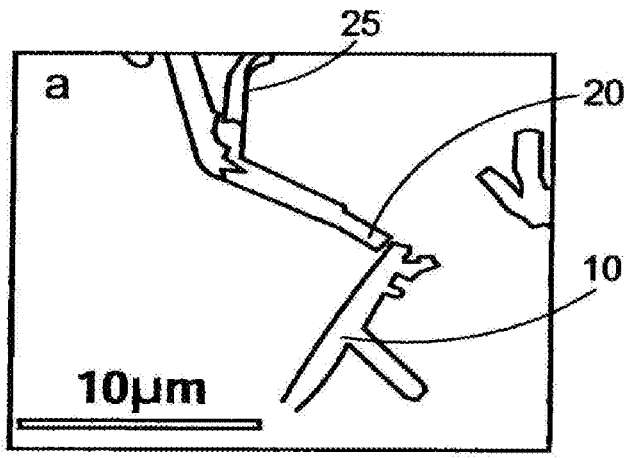
FIG. 3A is a drawing of a scanning electron microscopy (SEM) image showing a branched, tripod shaped ZnO nanorod transferred to $Si/SiO_2$ substrate and positioned using a FIB needle with intermediate connection from single ZnO nanorod.

The next step in our procedure is to scan the surface of the intermediate $Si/SiO_2$ substrate for conveniently placed ZnO nanorod-tripod. Then the needle 25 with attached single intermediate nanorod 20 is lowered and brought into the FIB focus and its tip positioned at the closed end of the branched nanorod 10 as shown in FIG. 3A. Before attaching a selected branched nanorod, it is recommended to push it in order to make sure that it is not attached firmly to the substrate and the branches are strong enough to be transferable.

Figure 3B:
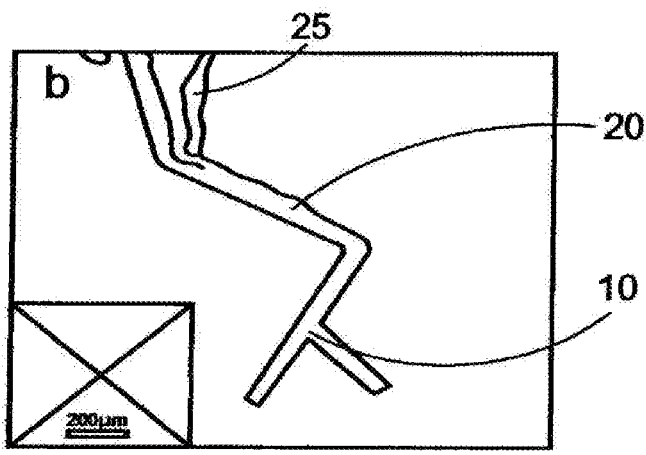
FIG. 3B is a drawing of a scanning electron microscopy (SEM) image showing branched, tripod shaped ZnO nanorod picked up by in-situ lift-out needle to be used as a tripod ZnO nanorod selected for nanofabrication, inset shows nanosensor substrate template (glass substrate with Al contacts as external electrodes).

Then the needle 25 with attached single intermediate nanorod 20 is lowered until it touches the tripod nanorod 10 and is attached to the end of the FIB needle as shown in FIG. 3B using Pt deposition of 0.5 mm thickness. Following the step shown in FIG. 3B, the needle 25, and specimen were moved away from the substrate.

Figure 3C:
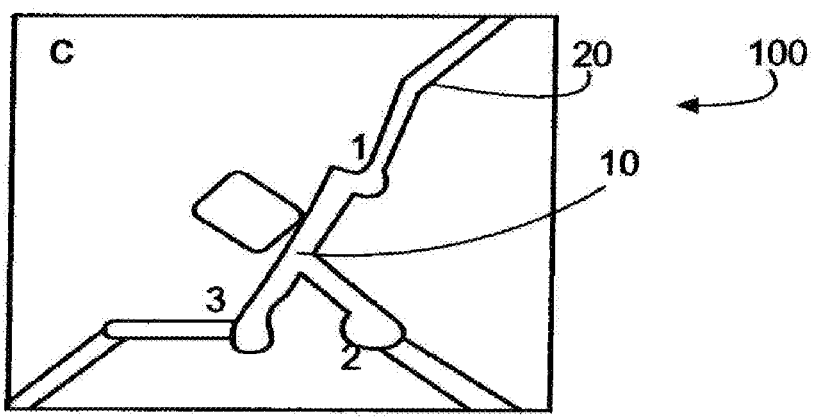
FIG. 3C is a drawing of a scanning electron microscopy (SEM) image showing a branched, tripod shaped nanorod cut from the FIB needle and brush touched to the sensor template support and fixed to three electrode/external connections as final nanosensor.

FIG. 3C shows the branched, tripod shaped nanorod 10 on the nanodevice substrate/template (see inset in FIG. 3B) with pre-deposited aluminum (Al) external electrodes 1, 2, and 3. In this step, the needle 25 with attached single intermediate nanorod 20 and with branched nanorod 10 is lowered and repeatedly swept across the substrate until branched nanorod 10 touches and brushes against the support and becomes attracted to it. If the nanorod does not initially lie flat on the substrate then it will be extremely difficult to realize good contacts with external electrodes. This situation will often happen in the case when an intermediate nanorod 20 is not used or if the selected nanorod is not flat to the intermediate Si/SiO$_2$ substrate (FIG. 3A). The last step consists of positioning of tripod nanorod 10, then fixed to one of the predeposited external electrodes. Then the branched nanorod 10 is cut from intermediate nanorod 20 and needle 25 and the intermediate nanorod 20 are raised away from the substrate.

FIG. 3C shows a single intermediate nanorod 20, ZnO branched, tripod shaped nanorod 10-based sensor 100 fabricated by nanotechnology. The typical time taken to perform this in-situ lift-out FIB nanofabrication is 30-45 minutes. Taking into account that nanorod synthesis was done in 10 minutes, the present invention overcomes the conception that single nanorod/nanowire is not convenient for sensor production as reported by C. Wang in *Sens. Actuators B* (2006), supra. To the contrary, the single nanorod/nanowire is quite useful in manipulation of the branched nanorod.

A detailed description of the fabrication technique makes it easier to learn and apply nanofabrication steps using easily transferable nanorods (avoiding nanorod agglomerations) fabricated by the method disclosed herein, especially for new users/operators and will permit the highest success rate. The success rate using the method disclosed herein is >90%. This minimizes the total time to machine time using FIB/SEM for the nanodevice fabrication and can be applied in other specific devices.

Example 2

In-Situ Lift-Out Procedure

The fabrication of a single ZnO nanorod hydrogen sensor using focused ion beam/scanning electron microscopy (FIB/SEM) in-situ lift-out technique is described below. The fabricated nanosensor can detect parts per million (ppm) level of hydrogen concentration at room temperature. The sensing material is single ZnO nanorod 30 which has been grown using a bio-safe aqueous solution method.

First, a microscope and a micromanipulator are used for the ex-situ lift-out technique and also used to separate individual ZnO nanorods in order to be easily attached to the in-situ FIB needle 25. A ×100 magnification was used to locate ZnO nanorods on the intermediate Si/SiO$_2$ substrate. A magnification of ×7000 was use to lift the single ZnO nanorod.

Then, a Keindiek Micromanipulator in the FIB/SEM system permits movements of a few nanometers along the x and y directions and 1 nm movements in the z direction. The Micromanipulator was mounted beside the stage. Next, the needles used for the lift-out step were electro-polished tungsten wire. Samples on the stage can be rotated, tilted perpendicular to either beam which enable easy arrangement of single ZnO nanorod on the nanosensor template (glass substrate with Al electrodes).

Figure 4:
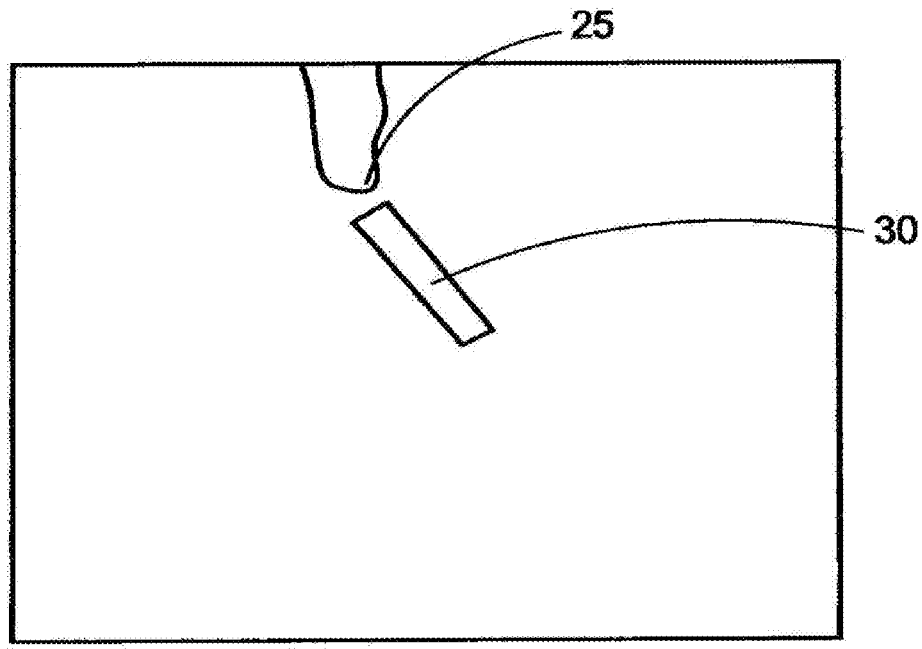
FIG. 4 is a drawing of a scanning electron microscopy (SEM) image showing a single, intermediate ZnO nanorod on Si substrate, next to the FIB needle.
Figure 5:
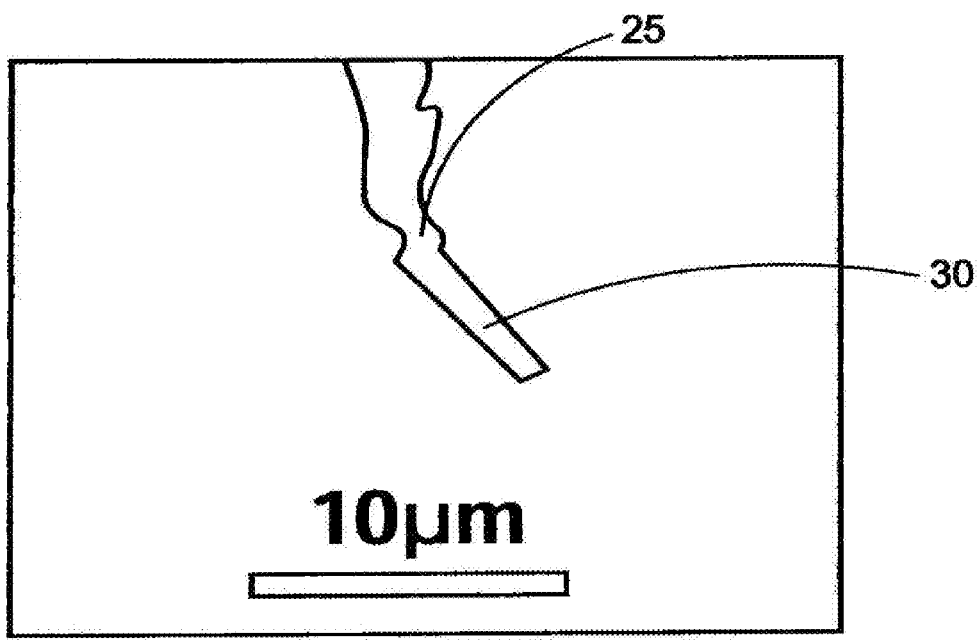
FIG. 5 is a drawing of a scanning electron microscopy (SEM) image showing a single, intermediate ZnO nanorod picked up by a FIB needle.

Following the selection of intermediate nanorods 30, in the in-situ lift-out process, the attachment of single intermediate nanorod 30 on the tip of the FIB needle 25 is shown in FIG. 4 and FIG. 5. Attachment of the FIB needle 25 to the single intermediate nanorod 30 will permit an easy pick-up of a second selected nanorod for further handling. This intermediary step makes it possible to fabricate nanodevices much faster.

During the attachment step, the needle 25 is lowered and its tip positioned at one end of an intermediate nanorod 30 as shown in FIG. 4.

The needle 25 is then moved until it touches the nanorod 30. Then the nanorod 30 is attached to the end of the FIB needle 25 as shown in FIG. 5 using Pt deposition.

Following the attachment step is scanning of the Si/SiO$_2$ substrate for well-placed ZnO nanorod. Once the desired nanorod is identified it is recommended to push the nanorod in order to make sure that it is not firmly attached to the substrate.

Figure 6:
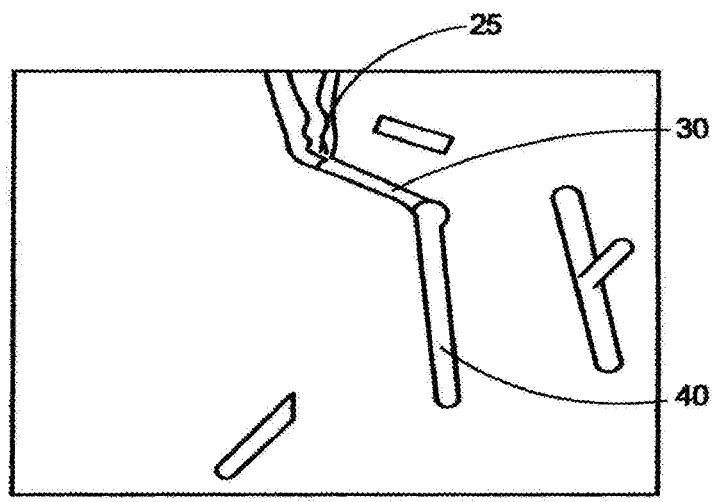
FIG. 6 is a drawing of a scanning electron microscopy (SEM) image showing a single ZnO nanorod selected for sensor fabrication.

After alignment of intermediate nanorod 30 with one end of the second selected nanorod 40, they were welded together with Pt deposition as shown in FIG. 6. Following this step the needle 25, single intermediate nanorod 30, and welded specimen 40 are raised away from the substrate.

Figure 7A:
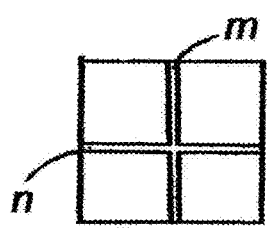
FIG. 7A is the inset in FIG. 7 showing the nanosensor substrate template with predeposited aluminum contacts as contact electrodes.
Figure 7:
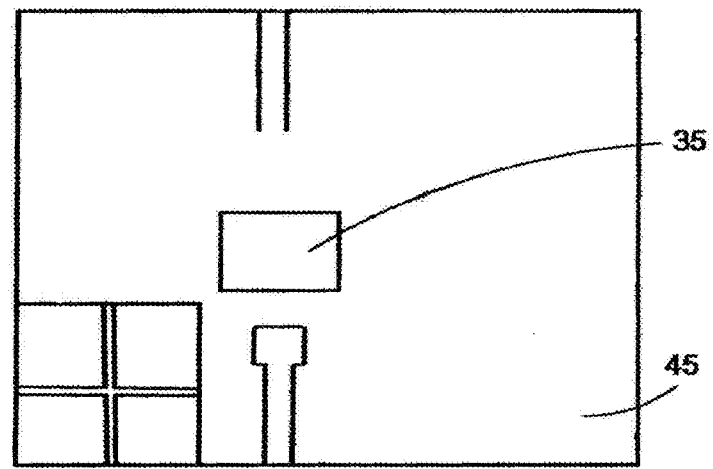
FIG. 7 is a drawing of a scanning electron microscopy (SEM) image showing a square hole cut on a glass substrate. Inset shows nanosensor substrate template (glass with Al contacts as contact electrodes).

A square cut is made on a substrate 45 to increase sensitivity two-fold. FIG. 7 shows a square hole 35 fabricated on the glass substrate 45 with Al external electrodes in order to allow entire surface of nanorod to be involved in the H$_2$ sensing process. FIG. 7A shows the detail of the predeposited aluminum external electrodes m is positioned vertically and n is positioned horizontally.

Figure 8:
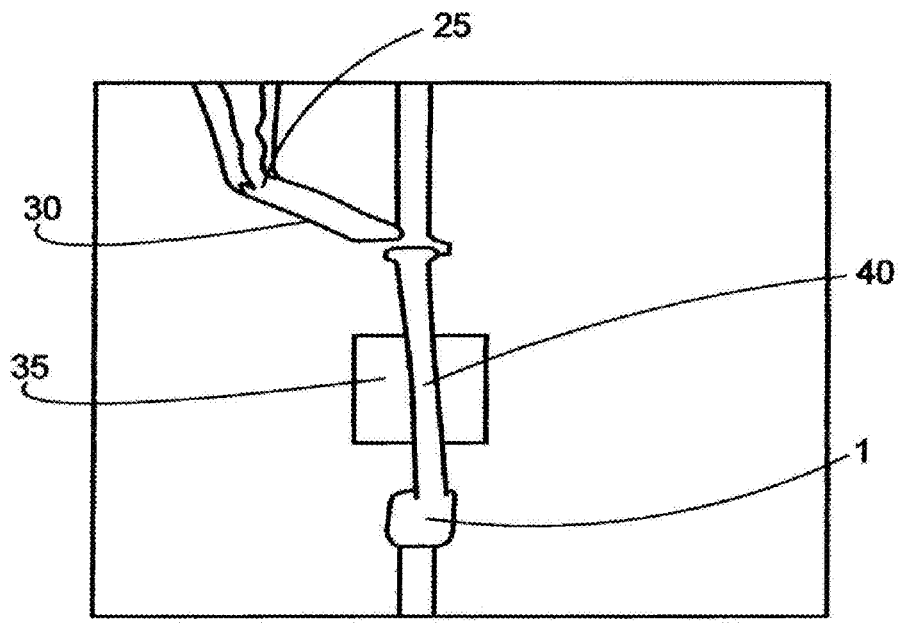
FIG. 8 is a drawing of a scanning electron microscopy (SEM) image showing the ZnO nanorod placed over the hole.

Then, using micromanipulator, the nanorod 40 is carefully positioned over the square hole 35 as shown in FIG. 8. In the last step, the nanorod is fixed to one of the pre-deposited electrodes/external contacts 1 as shown in FIG. 8. The ZnO nanorod 40 is cut from the intermediate single ZnO nanorod and the FIB needle 25 with attached single intermediate nanorod 30 are raised away from the substrate.

Figure 9:
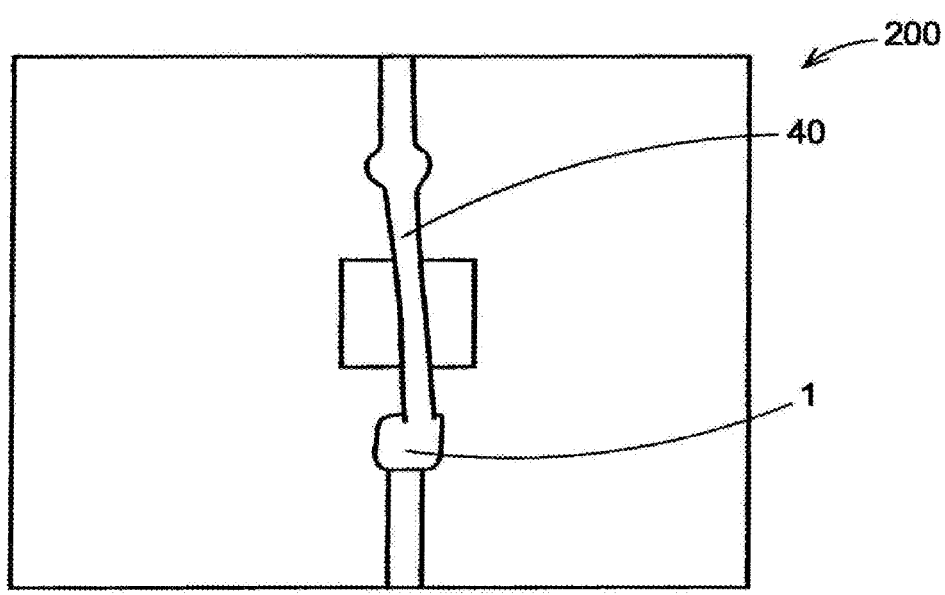
FIG. 9 is a drawing of a scanning electron microscopy (SEM) image showing a single nanorod welded to both electrode/external connections.

FIG. 9 shows the fabricated single nanorod-based nanosensor 200. The typical time to perform this in-situ lift-out FIB nanofabrication is about 20-30 minutes.

The fabricated single ZnO nanorod-based nanosensor 200 was tested in a 1000 cc test chamber to detect H$_2$. The ZnO sensor and its sensitivity to oxygen (O$_2$), methane (CH$_4$), carbon monoxide (CO), carbon dioxide (CO$_2$), and propane (LPG) gases at room temperature are also investigated. The readings are taken after a specific gas has been introduced into the chamber. It was found that resistance change $|\Delta R|=|R_{air}-R_{gas}|$ increased linearly with H$_2$ gas concentration.

Example 3

Gas Sensing Properties

Figure 10A:
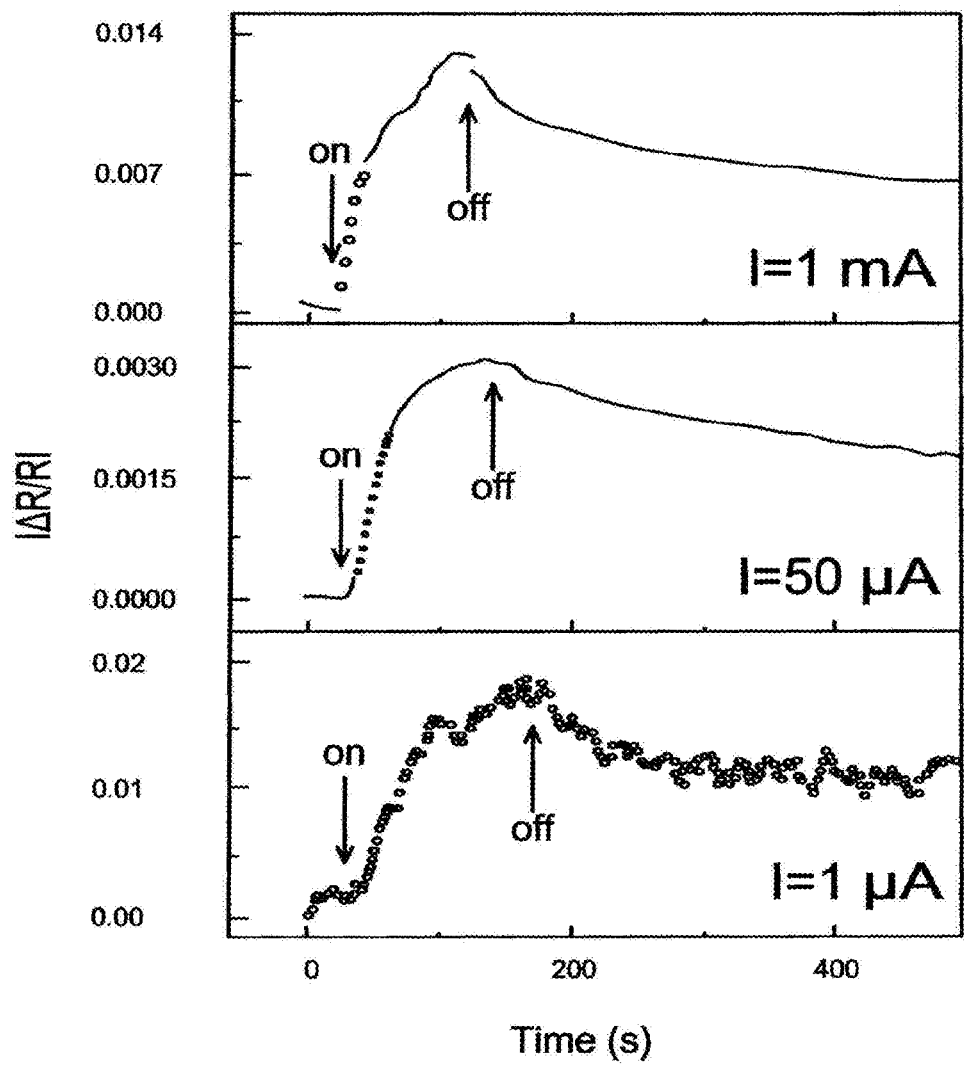
FIG. 10A is a graph of the room temperature relative response ($\Delta R/R$) of the single ZnO branched nanorod hydrogen nanosensor (shown in FIG. 3C) at different current values and directions between branches 1 and 2.
Figure 10B:
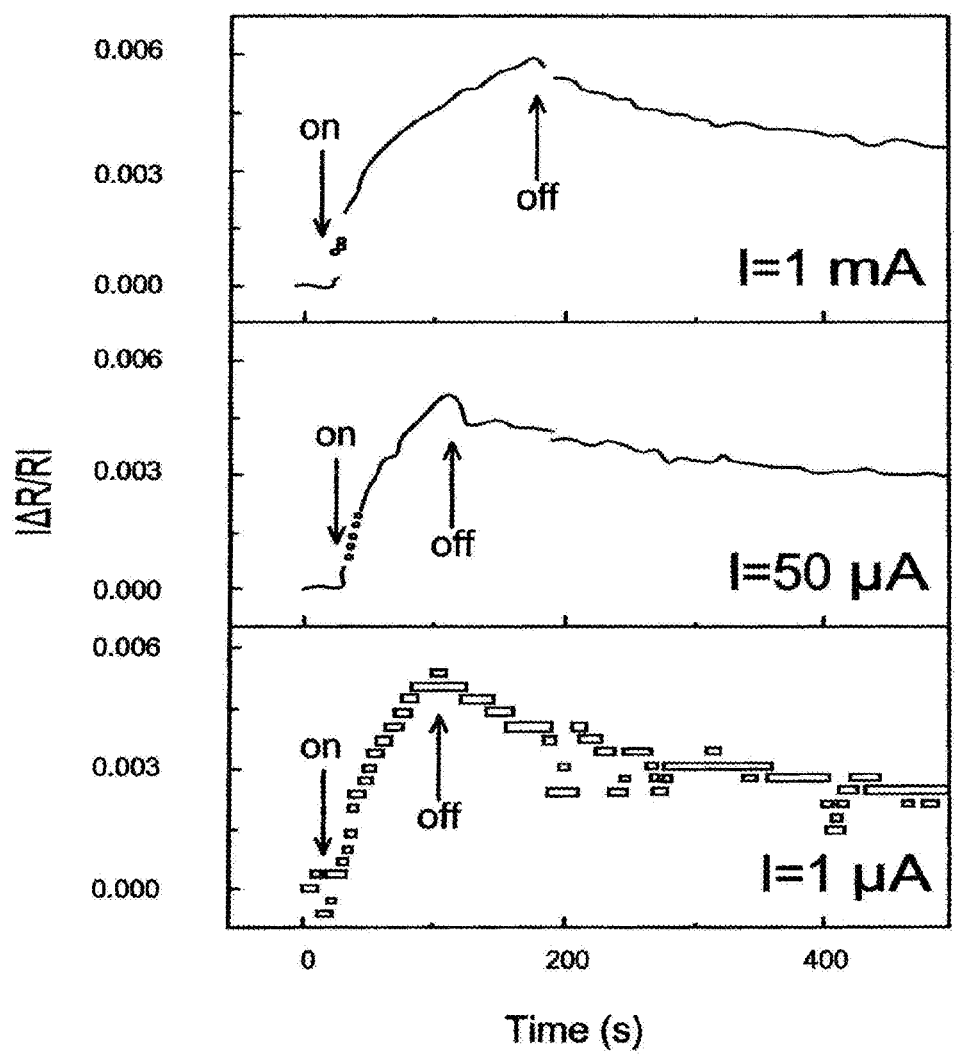
FIG. 10B is a graph of the room temperature relative response ($\Delta R/R$) of the single ZnO branched nanorod hydrogen nanosensor (shown in FIG. 3C) at different current values and directions between branches 1 and 3.
Figure 10C:
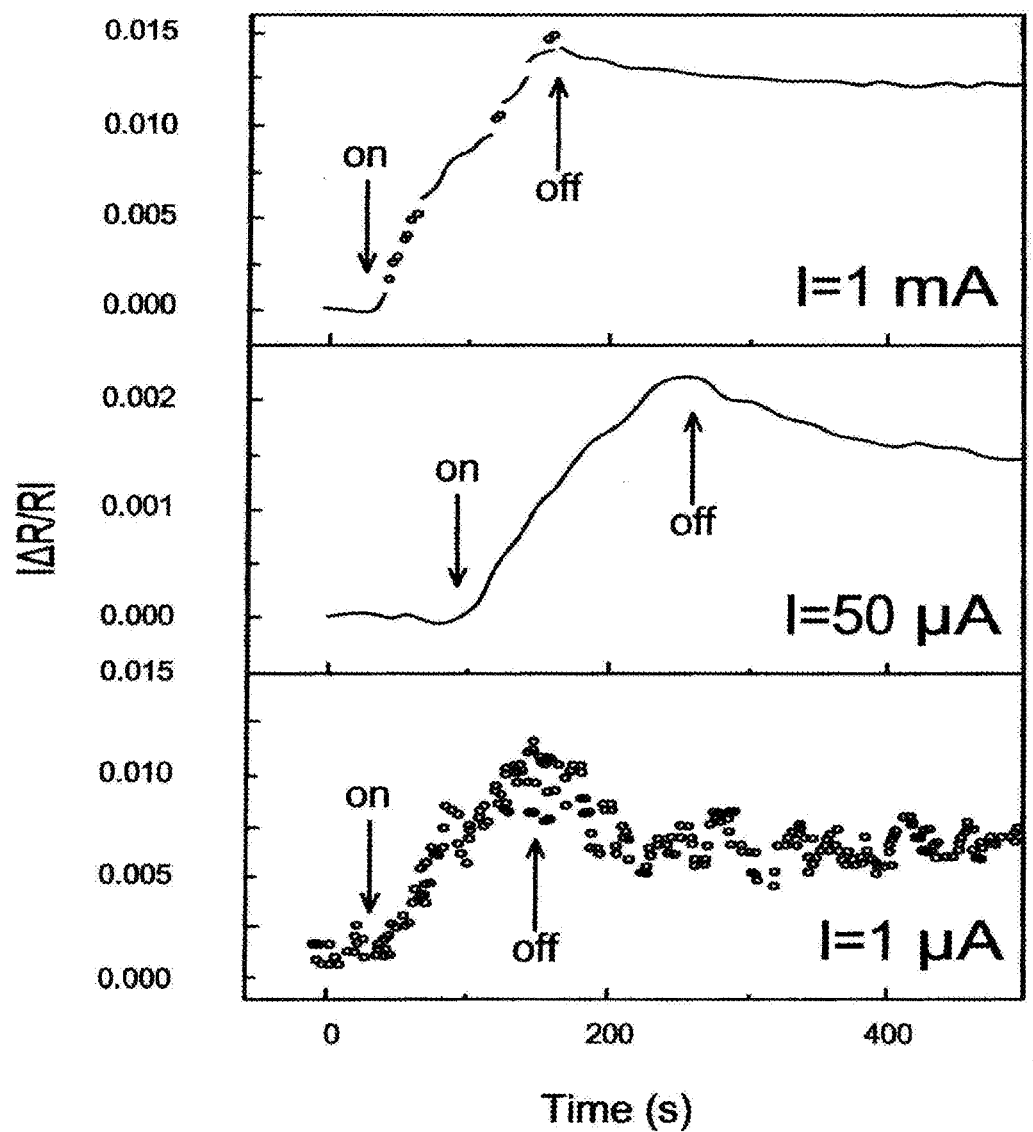
FIG. 10C is a graph of the room temperature relative response ($\Delta R/R$) of the single ZnO branched nanorod hydrogen nanosensor (shown in FIG. 3C) at different current values and directions between branches 2 and 3.

For gas sensing characterizations, the fabricated single ZnO branched nanorod sensor was placed in a 1000 cm$^3$ gas chamber and investigated sensitivity to H$_2$ and also O$_2$, CH$_4$, CO, CO$_2$ and LPG gases at room temperature in the concentrations up to 2000 ppm. The readings were taken after the gases have been introduced in the test chamber. It was found that resistance change $|\Delta R|=|R_{gas}-R_{air}|$ increased linearly with H$_2$ gas concentration and is constant for other gases at room temperature. The room temperature sensitivity of the self-assembled ZnO branched nanorod at 150 ppm H$_2$ is shown in FIGS. 10A, 10B and 10C for three different tripod connections. Sensitivity to hydrogen between branches 1 and 2 is shown in FIG. 10A; room temperature sensitivity to hydrogen between branches 1 and 3 is shown in FIG. 10B; and room temperature sensitivity to hydrogen between branches 2 and 3 is shown in FIG. 10C.

The relative resistivity changes after 50-80 s H$_2$ exposure becomes stable, on the other hand, the relative resistivity changes were not restored to the 90% of the original level within 5 min suggesting a relatively longer recovery time, in comparison with the response time of ~1 min. The sensor experiment is repeated for gas sensitivity to several common gases $O_2$, $CH_4$, CO, $CO_2$ and LPG under the same conditions and found that $|\Delta R/R|$ is less than 0.02% for these gases. By doping the ZnO nanorods with different impurities the nanorods are rendered sensitive to different gases. Therefore, we establish that the ZnO nanosensor has certain degree of selectivity.

The multiple pure ZnO nanorod-based sensor presented by H. T. Wang et al. in *Appl. Phys. Lett.* 86, supra has a sensitivity of ~0.25% at 500 ppm $H_2$ in $N_2$ after 10 min exposure. However, the Pd-coated ZnO nanowire gas sensors showed a higher $H_2$ sensitivity (4.2%) and fast response and recovery time at concentrations up to 500 ppm at the room temperature.

Furthermore a sensor based on ZnO multiple nanorods and exposed under 10% $H_2$ in $N_2$ at 112° C., showed high sensitivity ~18% of current change which are quite good.

By comparison, our single ZnO branched nanorod sensor exposed to 150 ppm $H_2$ shows a relative response ~2% in 50-80 seconds (s), while Rout et al. in *J. Phys. D: Appl. Phys.* 40, supra showed that single ZnO nanowire has a sensitivity of ~3 for 100 ppm $H_2$ at room temperature. The sensitivity $\Delta R/R$ of our sensor is attractive for further investigation for practical $H_2$ sensor applications.

Figure 11:
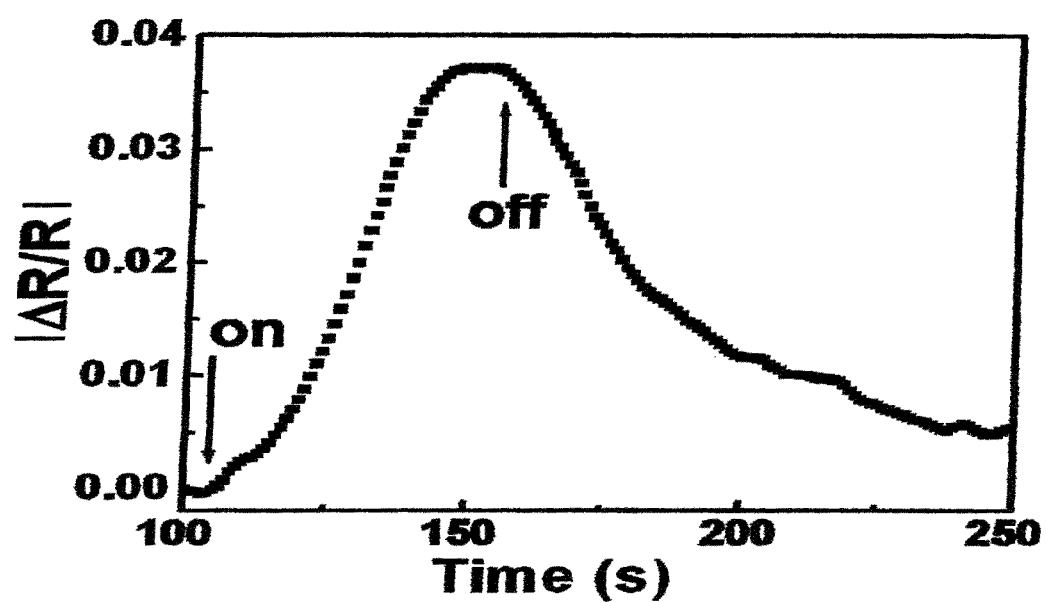
FIG. 11 is a graph of the room temperature sensitivity of a single nanorod ZnO nanosensor (shown in FIG. 9) when exposed to 200 ppm hydrogen gas over an approximately 150 second period of time with direct current turned on for the first 50 seconds.

With regard to a single nanorod nanosensor, after the exposure to hydrogen, the sensor is maintained for a recovering period in dry air. The room temperature sensitivity of the single nanorod ZnO nanosensor to 200 ppm $H_2$ is shown in FIG. 11. Response time constants are on the order of 30 seconds and after 40 seconds the signal reaches the equilibrium value after the $H_2$ test gas was injected. The relative resistance changes were about 4%. The resistance was restored toward the 10% above the original value within 50-90 sec of introducing clean air. This suggests a reasonable recovery time. The sensor showed relatively fast response and baseline recovery for 200 ppm $H_2$ detection at room temperature.

FIG. 11 shows the room temperature hydrogen gas sensitivity of a single nanorod nanosensor 200, as shown in FIG. 9, wherein over a 150 second period of time, hydrogen gas is detected within 50 seconds and baseline recovery occurs in approximately an additional 100 seconds.

The adsorption-desorption sensing mechanism is proposed on the basis of reversible chemisorption of the hydrogen on the ZnO nanorod. It produces a reversible variation in the resistivity with the exchange of charges between $H_2$ and the ZnO surface leading to changes in the depletion length as reported by H. L. Hartnagel et al in *Semiconducting Transparent Thin Films*, IOP, Bristol, 1995. Thus, one way to improve sensitivity is to increase the change in the surface/volume ratio as suggested by J. Riu et al., in "Nanosensors in environmental analysis," Talanta 69 (2) (2006) 288-301. It is well known that oxygen is adsorbed on a ZnO nanorod surface as $O^-$ or $O^{2-}$ by capturing electrons according to A. R. Raju et al in *Sens. Actuators* B3 (4) (1991) 305-310, S. Saito, et al in *J. Am. Ceram. Soc.* 68 (1985) 40-43, and S. Basu et al. in "Room-temperature hydrogen sensors based on ZnO," *Mater. Chem. Phys.* 47 (1997) 93-96. Hydrogen atoms react with these oxygen ions and produce water ($H_2O$) molecules $(O^-)_{ZnO} + 2H$ to yield $H_2O_{(g)} + e^-$ and the released electrons contribute to current increase through the nanorod. The reaction is exothermic in nature (1.8 kcal $mol^{-1}$) and the molecular water desorbs quickly from the surface as discussed by X.-J. Huang et al. in "Chemical sensors based on nonostructured materials," *Sens. Actuators B: Chem.* 122(2) (2007) 659-671.

In summary, an in-situ lift-out technique has been presented to fabricate single ZnO branched nanorod $H_2$ sensor. A self-assembled ZnO branched nanorod was also synthesized through a low-temperature aqueous solution route. The main advantage of the proposed synthesis is its simplicity and fast growth rates, 10 minutes versus several hours reported previously. An easy transfer of ZnO architectures to any substrate is shown and pick-up by using in-situ lift-out FIB, opening the possibility of reproducibly fabricating and studying novel nanosensor and nanodevices.

The typical time taken to perform this in-situ lift-out FIB nanofabrication is 30-45 minutes for branched nanorod sensor and 20-30 minutes for single straight nanorod nanosensor. Also take into account that nanorod synthesis takes about 10 minutes, and some obstacles, such as nanorod agglomeration, have been overcome for nanorods/nanowires sensor production.

The described technique makes it easier to learn and apply nanofabrication steps using easily transferable nanorods (avoiding nanorod agglomerations) fabricated by the method disclosed herein, especially for new users/operators, the present invention will permit the highest success rate. The process of the present invention achieved a success rate greater than 90%. This minimizes the total time to use FIB/SEM for the experimental nanodevice fabrication and can be extended for other specific devices.

The relative resistivity changes after 50-80 seconds of $H_2$ exposure becomes stable, but did not restore to the 90% of the original level within 5 minutes suggesting a relatively longer recovery time, in comparison with the response time of ~1 minute.

The fabricated single ZnO branched nanorod sensor has a relatively higher $H_2$ sensitivity (~2%) comparable to the multiple ZnO nanorod-based sensors. Also, gas selectivity to several common gases like $O_2$, $CH_4$, CO, $CO_2$, and LPG gases was identified, considering that relative response $|\Delta R/R|$ is less than 0.02% in the same conditions. This selectivity was found to be useful for further development of $H_2$ nanosensor at room temperature. The single ZnO branched nanorod sensor can gauge 150 ppm hydrogen gas in the air at room temperature and can operate at low power conditions, less than approximately 5 µW.

The fabrication method disclosed in the present invention is a bio-safe process that provides a hydrogen nanosensor which is efficient, operates on low power and has extremely small dimensions. Thus, a compact, reliable, inexpensive sensor device is now available that can detect hydrogen leaks. The sensor signal consists of relative resistance changes due to gas adsorption on the surface of nano-ZnO and permits real-time detection at room temperature.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A process for fabricating a zinc oxide nanorod hydrogen sensor using focused ion beam (FIB) in-situ lift-out technique, consisting essentially of:

mounting a micromanipulator with a focused ion beam (FIB) needle adjacent to a nanosensor template surface consisting of a glass substrate with at least two pre-deposited, external aluminum (Al) electrodes;

using a microscope and a micromanipulator to separate a plurality of individual zinc oxide nanorod structures formed on a first substrate surface;

using the micromanipulator to arrange one of the plurality of individual zinc oxide nanorod structures on the nanosensor template surface by contacting the individual zinc oxide nanorod structure with the tip of an FIB needle on the first substrate surface where the plurality of zinc oxide nanorod structures are formed;

attaching a first intermediate straight zinc oxide nanorod linearly to the tip of the FIB needle, then linearly attaching a second selected zinc oxide nanorod to the intermediate zinc oxide nanorod;

raising the FIB needle and thereby moving the attached first intermediate zinc oxide nanorod and the second selected zinc oxide nanorod onto the nanosensor template with at least two pre-deposited external electrodes;

positioning the second selected zinc oxide nanorod on the nanosensor template and fixing the second selected zinc oxide nanorod to at least one of the predeposited external electrodes of the nanosensor template;

separating the first intermediate zinc oxide nanorod from the second selected zinc oxide nanorod that is fixed to at least one electrode of the nanosensor template;

lifting the FIB needle and the attached first intermediate single zinc oxide nanorod away from the nanosensor template; and thereby fabricating a room temperature, zinc oxide nanorod based hydrogen gas sensor on the nanosensor template surface.

2. The process of claim 1, wherein the attaching of the first intermediate straight zinc oxide nanorod linearly to the tip of the FIB needle is by platinum (Pt) deposition welding.

3. The process of claim 1, wherein the attaching of the second selected zinc oxide nanorod to the intermediate zinc oxide nanorod is by platinum (Pt) deposition welding.

4. The process of claim 1, wherein the second selected zinc oxide nanorod is at least one of a single, straight zinc oxide nanorod and a branched, tripod-shaped zinc oxide nanorod.

5. The process of claim 1, further includes cutting a square hole in the nanosensor template to increase the sensitivity of the zinc oxide nanorod-based nanosensor.

6. The process of claim 5, wherein the micromanipulator places the second selected zinc oxide nanorod over the square hole in the nanosensor template.

7. The process of claim 4, wherein the zinc oxide nanorod nanosensor template has three electrode connections for attachment of the branched, tripod-shaped nanorod to detect hydrogen gas at room temperature.

8. The process of claim 1, wherein the zinc oxide hydrogen gas nanosensor is fabricated in a time period ranging from approximately 30 to approximately 45 minutes.

* * * * *